United States Patent [19]

Furubayashi et al.

[11] Patent Number: 4,651,121
[45] Date of Patent: Mar. 17, 1987

[54] MOISTURE SENSOR AND A METHOD FOR THE PRODUCTION OF THE SAME

[75] Inventors: Hisatoshi Furubayashi; Masaya Hijikigawa, both of Nara, Japan

[73] Assignee: Sharp Kabushiki Kaisha, Osaka, Japan

[21] Appl. No.: 733,466

[22] Filed: May 13, 1985

[30] Foreign Application Priority Data

May 15, 1984 [JP] Japan .................................. 59-97879

[51] Int. Cl.⁴ .......................... H01L 7/00; H01G 5/20
[52] U.S. Cl. ........................................ 338/35; 338/34; 361/286
[58] Field of Search ..................... 338/34, 35; 361/286, 361/280, 304; 428/636, 432

[56] References Cited

U.S. PATENT DOCUMENTS 3,380,136  4/1968  Wydro, Sr. ...................... 361/304 X
3,984,907 10/1976  Vossen, Jr. et al. ............. 428/636 X
4,164,868  8/1979  Suntola ........................... 361/286 X

FOREIGN PATENT DOCUMENTS 2759989  8/1978  Fed. Rep. of Germany .
55-95857  7/1980  Japan .

Primary Examiner—E. A. Goldberg
Assistant Examiner—Linda M. Peco
Attorney, Agent, or Firm—Spencer & Frank

[57] ABSTRACT

A moisture sensor comprising a substrate; a bottom electrode on the substrate; a moisture sensitive film sandwiched between an upper electrode and the bottom electrode on the substrate; a pair of connection terminals one of which is extended on the substrate from the bottom electrode and the other of which is formed on the substrate to be connected to the upper electrode; a step-shaped extension extended on the end of the moisture sensitive film from the upper electrode to the connection terminal for the upper electrode; and a metal film which covers said step-shaped extension.

5 Claims, 5 Drawing Figures

MOISTURE SENSOR AND A METHOD FOR THE PRODUCTION OF THE SAME

BACKGROUND OF THE INVENTION

1. Field of the Invention

This invention relates to a moisture sensor and a method for the production of the same. More particularly, it relates to a technique for the formation of electrodes of a moisture sensor.

2. Description of the Prior Art

Moisture sensors having a variety of moisture sensitive materials such as metal oxides, polymer materials, etc., have been developed as sensor means for detecting humidity and have the possibility of an enlarged range of applications with regard to air-conditioning machinery, medical treatment apparatus, automobiles, agriculture and forestry machinery, etc. These moisture sensors are roughly classified into two groups, one of which is a resistance-variation format including moisture sensors having a moisture sensitive material such as $Fe_2O_3$, $SnO_2$, LiCl, etc. This resistance-variation format is based on the fact that the electroconductive properties of various ions, protons, electrons, etc., in the moisture sensitive material vary depending upon a variation in water-content therein. The other group is of an electrostatic capacitance-variation format including moisture sensors having a moisture sensitive material such as $Al_2O_3$, cellulose, etc. This electrostatic capacitance-variation format is based on a characteristic that the dielectric constant of the moisture sensitive material varies depending upon a variation in the water-content therein resulting in a variation of the electrostatic capacitance. There have been exceptional moisture sensors, having a moisture sensitive material such as certain polymers (e.g., polyvinylalcohol), which function as either an electrostatic capacitance-variation format sensor or a resistance-variation format sensor depending upon the range of humidity to be detected.

Electrostatic capacitance-variation type moisture sensors are advantageous over resistance-variation type moisture sensors in that the moisture sensitive characteristic of the electrostatic capacitance-variation type sensors varies linearly with relative humidity and exhibits almost no variation with changes in temperature.

In order to utilize the characteristics of the above-mentioned various kinds of moisture sensors, an electrode structure which is suitable for the characteristic of each of these sensors must be designed. To the conventional moisture sensors having a moisture sensitive material in a thin film formed on an insulating substrate, the following two kinds of electrode structure have been applied:

One of the two kinds of electrode structure is a comb-shaped structure comprising a pair of comb-shaped electrodes and a moisture sensitive film on the comb-shaped electrodes to electrically connect the comb-shaped electrodes with each other. The electrodes are disposed on a substrate by a vacuum evaporation technique or a screen printing method in a manner that each of the protrusions of one of the comb-shaped electrodes faces the concave surface of the other. Such a comb-shaped structure is generally applied to resistance-variation type moisture sensors, the electrodes of which are formed before the formation of the moisture sensitive film so that the desired material for electrodes having an excellent adherence to the substrate can be selected.

The other electrode structure is a triple-layered structure which comprises an upper electrode, a bottom electrode and a moisture sensitive film sandwiched between these electrodes, resulting in a large electrostatic capacitance. Such a triple-layered structure is generally used for electrostatic capacitance-variation type moisture sensors, in which an extremely thin film of a noble metal such as Au, Pt, etc., is used as the upper electrode which must have moisture permeability and corrosion resistance. Such a noble metal thin film is inferior in adherence to the substrate thereby making difficult the drawing of a lead wire therefrom. When a lead wire is connected to the thin noble metal film by means of an Ag paste, etc., the area of the noble metal film sticks to the substrate which corresponds to the connecting portion of the noble metal film, and the lead wire becomes weak causing ready separation of the noble metal film from the substrate and/or breaking thereof. In order to eliminate such problems in actual use, the following approaches for attaching the noble metal film to the substrate have been proposed:

(1) an approach in which the noble metal film is pressed to the substrate by a metal board or a metal ring;

(2) an approach in which the moisture sensitive film is formed on the bottom electrode divided into two parts and the extremely thin electrode film which is moisture permeable is formed on the moisture sensitive film, and then the lead wires, respectively, are connected to the two parts of the bottom electrode; and (3) an approach in which a portion of the upper electrode is extended to a connection terminal on a substrate on the outside of the moisture sensitive film having a pattern and a lead wire is drawn from the connection terminal.

The first approach mentioned in Item (1) has a problem in that the electrode structure is complicated so that the electrodes tend to be damaged in the assembly process. The second approach mentioned in the Item (2), although having no problems in the production process, is not compact due to reduced moisture sensitivity resulting from such an electrode structure. This is because the equivalent network thereof indicates that, as compared with an equivalent network of a different electrode structure having a non-divided bottom electrode on a substrate, two halves of the electrostatic capacitance (C/2) of the moisture sensitive film are connected to each other in series resulting in a one fourth electrostatic capacitance of the moisture sensitive film (represented by the formula:

$$C = \frac{C/2 \times C/2}{C/2 + C/2} = \frac{C}{4})$$

per effective area of the substrate produced by the equivalent network indicated by the above-mentioned different electrode structure.

The third approach mentioned in the Item (3) has the problems that adherence between the substrate and the noble metal thin film is weak in the case where the surface of the substrate is smooth, such as a glass substrate, a Si substrate coated with $SiO_2$, $Si_3N_4$, etc. and the like and the step portions in the pattern of the moisture sensitive film tend to be broken.

SUMMARY OF THE INVENTION

The moisture sensor of this invention which overcomes the above-discussed disadvantages and other numerous drawbacks of the prior art, comprises a substrate; a bottom electrode on the substrate; a moisture sensitive film sandwiched between an upper electrode and the bottom electrode on the substrate; a pair of connection terminals one of which is extended on the substrate from the bottom electrode and the other of which is formed on the substrate to be connected to the upper electrode; a step-shaped extension positioned over the end of the moisture sensitive film from the upper electrode to the connection terminal for the upper electrode; and a metal film which covers said step-shaped extension.

The bottom electrode and said connection terminal for the upper electrode are made of a double-layered metal film, which is, in a preferred embodiment, composed of a lower layer having sufficient adhesion to the substrate and an upper layer having sufficient moisture and corrosion resistance. The lower layer is made of at least one metal selected from Ni, Cr and Mn and said upper layer is made of at least one of Au and Pt.

The upper electrode is a moisture permeable thin film made of a noble metal. The metal film, which covers the step-shaped extension from the upper electrode to the connection terminal of the bottom electrode, is made of a noble metal.

The method for the production of the moisture sensor of this invention which also overcomes the above-discussed disadvantages and other numerous drawbacks of the prior art, comprises (1) disposing a metal film on a substrate,
(2) subjecting said metal film to a patterning treatment to form a bottom electrode and a pair of connection terminals, one of which is extended from the bottom electrode and the other of which is to be connected to an upper electrode,
(3) disposing a moisture sensitive film on said bottom electrode,
(4) disposing said upper electrode on said moisture sensitive film to connect a step-shaped extension protruding from said upper electrode to said connection terminal on the substrate for the upper electrode, and
(5) covering said step-shaped extension with a metal film.

Thus, the invention described herein makes possible the objects of (1) providing a moisture sensor, the electrodes of which neither separate from the substrate nor break due to the use of a novel electrode formation technique; (2) providing a moisture sensor having an upper electrode which is excellent in toughness, reliability and producibility of the connection portion thereof to a lead wire retaining the moisture permeability of the upper electrode; (3) providing a moisture sensor which is not only of a compact type, but which also has a large electrostatic capacitance since the whole area of the moisture sensitive film used therein can be effectively used.

BRIEF DESCRIPTION OF THE DRAWINGS

This invention may be better understood and its numerous objects and advantages will become apparent to those skilled in the art by reference to the accompanying drawings as follows.

DESCRIPTION OF THE PREFERRED EMBODIMENTS

Figure 1:
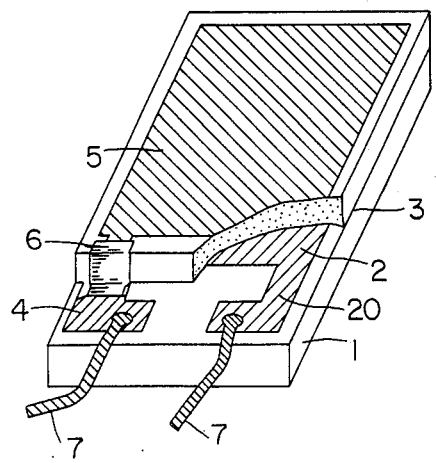
FIG. 1 is a partly sectional perspective view of a moisture sensor according to this invention.
Figure 2A:
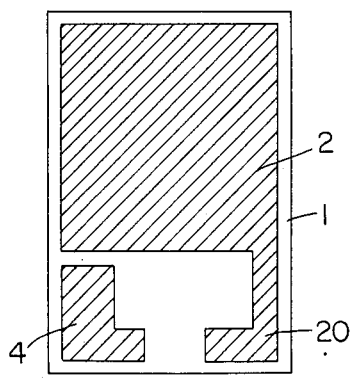
FIGS. 2(A) to (D) are plan views illustrating a manufacturing process of a moisture sensor according to this invention.

FIG. 1 shows an electrostatic capacitance-variation type moisture sensor of this invention, which has a triple-layered structure comprising a pair of thin electrode films 2 and 5 with a moisture sensitive thin film 3 being sandwiched between the thin electrode films 2 and 5 on a substrate 1. The surface of the substrate 1 must be smooth, examples of which are a glass substrate, a Si substrate coated with a $SiO_2$ film, a $Si_3N_4$ film or the like, and a polished alumina substrate. As shown in FIG. 2(A), a bottom electrode 2 is formed on the substrate 1, first. The bottom electrode 2 must be excellent in adherence to the substrate 1 and in moisture and corrosion resistance. In order to meet these requirements, a multiple-layered metal film is preferably formed as the bottom electrode 2 on the substrate 1 by means of a vacuum evaporation technique, a sputtering method, etc. The multiple-layered metal film is, for example, composed of a lower layer made of a metal film such as Ni, Cr, Mn, etc., which is active and excellent in adhesion to the substrate, and an upper layer made of a noble metal film such as Au, Pt, etc., which is excellent in moisture and corrosion resistance.

The bottom electrode 2 is then subjected to a patterning treatment by a masking evaporation technique, an etching technique, a lift off technique, etc. in a manner to form an L-shaped connection terminal 20 in one corner to be connected to a lead wire 7 and the other L-shaped connection terminal 4 in the other corner to be connected to the upper electrode 5 and a lead wire 7. These L-shaped connection terminals 4 and 20 are symmetrical about the center line of the bottom electrode.

The resulting connection terminal 4 for both the upper electrode 5 and the lead wire 7 is made of the same double-layered metal film as the bottom electrode 2 on the substrate 1. It should be understood that the connection terminal 4 must be patterned in such a manner that the end part thereof is sandwiched between a portion of the lower face of the moisture sensitive film 3 and a portion of the upper face of the substrate 1 to prevent a portion of the upper electrode 5 from contacting the substrate 1 when the upper electrode 5 is connected to the connection terminal 4 and that the connection terminal 4 is not in contact with the bottom electrode 2.

Figure 2B:
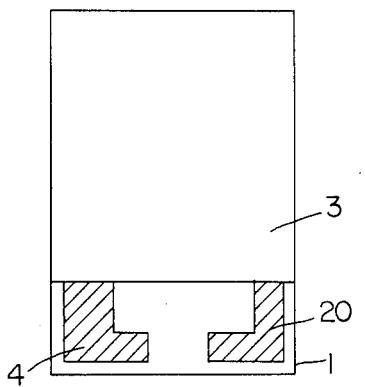

On the substrate 1 having the bottom electrode 2 and the connection terminal 4 thereon, as shown in FIG. 2(B), the moisture sensitive film 3 is then formed to cover the whole region of the bottom electrode 2 except the connection terminals 4 and 20 in such a manner that an organic polymer solution which is prepared by dissolving a polymer material such as polyvinyl alcohol, polystyrene sulfonate, polyacrylate, etc., in a solvent, is coated on the bottom electrode 2 and the substrate 1 by a spin casting technique followed by a heat-drying treatment and an etching treatment.

Figure 2C:
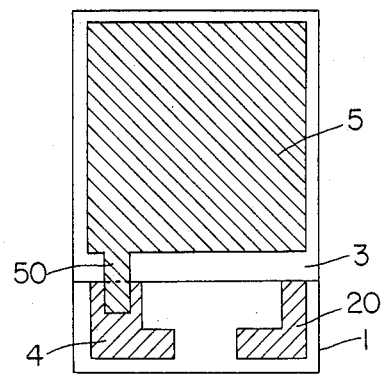

On the moisture sensitive film 3, as shown in FIG. 2(C), an extremely thin film which is moisture permeable and made of a noble metal such as Au, Pt, etc. is formed as the upper electrode 5 having an extension 50.

Figure 2D:
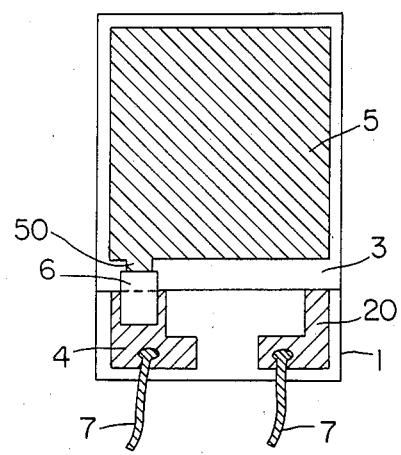

The extension 50 is bent at the edge of the moisture sensitive film 3 in a step-shape to be connected to the connection terminal 4. The width of the extension 50 is narrower than that of the connection terminal 4. The upper electrode 5, having a thickness of several hundred Ångströms, is extremely thin to attain an excellent moisture permeability, so that the extension 50 connecting the body of the upper electrode 5 to the connection terminal 4 tends break in the step-portion around the end of the moisture sensitive film 3. In order to eliminate the breaking of the extension 50, the step-portion of the extension 50 is covered with a noble metal film 6 made of Au, Pt, etc. having a certain thickness. From the connection terminals 4 and 20, lead wires 7 are drawn by means of a wire bonding technique, a welding technique, etc., resulting in a moisture sensor shown in FIG. 2(D).

The moisture sensor obtained above, which utilizes the moisture absorption and the ionic conductivity of the moisture sensitive film 3, detects humidity in the atmosphere as follows:

When water vapor in the atmosphere permeates into the moisture sensitive film 3 through the upper electrode 5, the process of the water-molecule absorption to or the water-molecule desorption from the film 3 is reversible resulting in a variation of the dielectric constant or the electrostatic capacitance. When an electric current flows into the film 3 through the upper electrode 5 and the bottom electrode 2, the electric conductance of the film 3 varies with a variation of the electrostatic capacitance of the film 3 so that the amount of water vapor in the atmosphere can be determined by this moisture sensor by detecting the variation of the electric conductance using a detecting circuit connected to the lead wires 7.

The moisture sensor of this invention is not limited to one unit for a substrate, but a number of moisture sensor units can be formed in a row for the same substrate, each of which is uniform in quality. Moreover, the production of the moisture sensor does not include a process at a high temperature and the formation of the electrodes and the disposition of the lead wires can be achieved using the conventional thin-film formation technique, thereby attaining minimization of the production cost and the size and weight of the moisture sensor.

Instead of the insulating substrate 1, a substrate including a field effect transistor (FET) therein can be used to provide a moisture sensor, having the above-mentioned electrodes and moisture sensitive film on the gate insulating film in the FET, which is operated by the FET. This allows for the incorporation of the relative circuits into the moisture sensor resulting in an advanced integration of circuits.

As the moisture sensitive film 3, a polymer film made of acetate, cellulose, nylon or the like, a metal oxide film made of $Al_2O_3$ or the like, etc., can be employed. Instead of the multiple-layered metal film for the bottom electrode 2, an Ag paste, a ruthenium oxide paste, etc., can be applied to the substrate 1 followed by a baking treatment to form the bottom electrode 2.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty which reside in the present invention, including all features which would be treated as equivalents thereof by those skilled in the art to which this invention pertains.

What is claimed is:

1. A moisture sensor comprising: a substrate; a bottom electrode disposed on the substrate; an upper electrode; a moisture sensitive film sandwiched between said upper electrode and the bottom electrode on said substrate; a pair of connection terminals one of which is extended on the substrate from the bottom electrode and the other of which is formed on the substrate to be connected to the upper electrode, said bottom electrode and said connection terminal for said upper electrode being made of a double-layered metal film which is composed of a lower layer having sufficient adhesion to said substrate and an upper layer having sufficient moisture and corrosion resistance; a step-shaped extension extended on an end of said moisture sensitive film from said upper electrode to said connection terminal for said upper electrode; and a metal film which covers said step-shaped extension.

2. A moisture sensor according to claim 1, wherein said lower layer is made of at least one material selected from Ni, Cr and Mn and said upper layer is made of at least one of Au and Pt.

3. A moisture sensor according to claim 1, wherein said upper electrode is a moisture permeable thin film made of a noble metal.

4. A moisture sensor according to claim 1, wherein said metal film, which covers the step-shaped extension from the upper electrode to the connection terminal of the bottom electrode, is made of a noble metal.

5. A moisture sensor comprising:
a substrate;
first and second electrodes, said first electrode being disposed on said substrate;
a moisture sensitive film having an end surface and being sandwiched between said first and second electrodes;
first and second connection terminals disposed on said substrate, said first connection terminal comprising an extension of said first electrode and said second connection terminal being separated from said first electrode, said first electrode and said second connection terminal each being made of a double-layered metal film including a lower layer having sufficient adhesion to said substrate and an upper layer having sufficient moisture and corrosion resistance;
a step-shaped extension extended on the end surface of said moisture sensitive film from said second electrode to said second connection terminal; and
a metal film covering said step-shaped extension.

* * * * *